(12) United States Patent
Dickinson et al.

(10) Patent No.: US 8,118,742 B2
(45) Date of Patent: Feb. 21, 2012

(54) INTRAVASCULAR ULTRASONIC CATHETER ARRANGEMENTS

(75) Inventors: Robert Dickinson, London (GB); Elvin Nix, Monmouth (GB)

(73) Assignee: Volcano Corporation, Rancho Cordova, CA (US)

( * ) Notice: Subject to any disclaimer, the term of this patent is extended or adjusted under 35 U.S.C. 154(b) by 1256 days.

(21) Appl. No.: 10/398,967

(22) PCT Filed: Oct. 11, 2001

(86) PCT No.: PCT/GB01/04548
§ 371 (c)(1),
(2), (4) Date: Dec. 17, 2004

(87) PCT Pub. No.: WO02/32315
PCT Pub. Date: Apr. 25, 2002

(65) Prior Publication Data
US 2006/0052707 A1 Mar. 9, 2006

(30) Foreign Application Priority Data
Oct. 14, 2000 (GB) .................................. 0025250.2

(51) Int. Cl.
*A61B 8/00* (2006.01)
(52) U.S. Cl. ......... 600/437; 600/447; 600/463; 600/466
(58) Field of Classification Search .................. 600/437, 600/447, 463, 466
See application file for complete search history.

(56) References Cited

U.S. PATENT DOCUMENTS

| 4,841,977 | A | * | 6/1989 | Griffith et al. | 600/439 |
| 4,917,097 | A | * | 4/1990 | Proudian et al. | 600/463 |
| 5,060,651 | A | * | 10/1991 | Kondo et al. | 600/443 |
| 5,226,847 | A | * | 7/1993 | Thomas et al. | 600/463 |
| 5,345,139 | A | | 9/1994 | Gururaja et al. | |
| 5,744,898 | A | * | 4/1998 | Smith et al. | 310/334 |
| 5,947,905 | A | * | 9/1999 | Hadjicostis et al. | 600/463 |
| 6,499,348 | B1 | * | 12/2002 | Mamayek | 73/632 |
| 6,605,043 | B1 | * | 8/2003 | Dreschel et al. | 600/459 |

FOREIGN PATENT DOCUMENTS

| EP | 0671221 A | 9/1995 |
| EP | 0671221 B1 * | 9/1995 |

OTHER PUBLICATIONS

Cronje et al., High-Permittivity Ceramic Dielectrics for Tuning Transmission in Power Electronic Converters, 1992 IEEE, pp. 601-606.*
International Search Report, dated Jan. 31, 2002, in corresponding PCT Application No. PCT/GB01/04548.

* cited by examiner

*Primary Examiner* — Long V. Le
*Assistant Examiner* — Ellsworth Weatherby
(74) *Attorney, Agent, or Firm* — Haynes and Boone, LLP (57) ABSTRACT

Apparatus for intravascular ultrasonic imaging comprises a catheter having an ultrasonic transducer array fabricated at least in part from an electrostrictive material, wherein the electrostrictive material is non-polymeric.

22 Claims, 5 Drawing Sheets

INTRAVASCULAR ULTRASONIC CATHETER ARRANGEMENTS

AREA OF THE INVENTION

The present invention relates to intravascular ultrasonic catheter arrangements and more particularly to the construction and manufacture of an ultrasonic transducer array for mounting at or near the distal end of a catheter arrangement.

BACKGROUND OF THE INVENTION

Examples of the types of intravascular ultrasonic catheter arrangements to which the present invention may be applied are disclosed in our earlier United Kingdom Patent Nos. 2,221,267; 2,233,094 and our U.S. Pat. Nos. 5,081,993; 5,257,629 and 5,456,259.

With the kinds of ultrasonic transducer array to which the present invention relates, its very small size (typically one millimetre in diameter) means that there are considerable technological problems to overcome in order to firstly make it possible to manufacture the array at an acceptable yield level and secondly to provide the array and its associated control circuitry/software with an acceptable performance particularly as far as the definition of images obtained is concerned.

Ultrasound arrays to which the present invention is applicable have typically employed piezoelectric materials such as modified PZT (lead zirconate titanate) for the transduction of a radio frequency (rf) electrical signal into an ultrasonic signal. In very high frequency applications, such as are relevant to the present invention, the performance of such piezoelectric arrays is limited by the grain size of the piezoelectric ceramic material. This is because, due to the very small size of the array, the grain size of the material begins to become comparable with the dimensions of the array elements.

Furthermore, because of the crystalline nature of the material from which the elements of the array are manufactured, the manufacturing operations such as lapping, polishing, dicing and electroding (i.e. securing electrodes to the elements of the array) introduce defects which are associated both with the bulk body of the transducer element material and its surface. In particular microcracks are generated which significantly reduce the macroscopic fracture resistance of the material.

SUMMARY OF THE INVENTION

One object of the present invention therefore is to overcome or reduce the above mentioned manufacturing problems whilst at the same time not prejudicing the operational performance of the ultrasonic transducer arrangement.

In order to try and overcome the above discussed problems the inventors have therefore researched alternative materials for the manufacture of ultrasonic transducer elements and have concluded that a class of materials that would be suitable are those known as electrostrictive materials such as "relaxor ferroelectrics".

It has been found that these can exhibit a large pseudo-piezoelectric response if a suitable d.c. electric bias field is applied to them. These materials have a finer microstructure than the known PZT material discussed earlier together with enhanced fracture toughness. An example of a relaxor ferroelectric material is modified PMN (lead magnesium niobate).

As indicated these relaxor ferroelectrics can exhibit a very large pseudo piezoelectric response, typically $d_{33}$–3,000 pC/N. In addition such materials are available with high values of permittivity (e.g. $e_r$-12000), with small grain size (e.g. 1-2 µm) and with improved fracture toughness.

High values of permittivity will, in general, allow improved ultra-small array elements from the interrogating electronics by reducing the element impedance.

Fine grain microstructures will reduce surface microcrack dimensions and thus the overall tendency to fracture. A further advantageous feature of an electrostrictive material is that it is unpolarised in the absence of the bias field. This means that processing steps involving heat and high local stresses will not result in the polarising degradation which can occur with piezoelectric materials such as PZT.

Thus according to a first aspect of the present invention, in an ultrasonic transducer array arrangement suitable for mounting on a catheter, the elements of the transducer array are manufactured from a non-polymeric electrostrictive material.

According to a second aspect of the present invention the control arrangement for energising such an array and processing signals derived therefrom comprises means for applying a bias voltage to the elements of the array, to render those elements significantly piezoelectric, and means for transmitting and receiving signals in relation to those transducer elements only when the bias voltage is being applied.

With this arrangement it is thus possible to apply the rf signals simultaneously (but not continuously) to all elements of the array because only those transducer elements which have the bias field applied to them will transform the rf signal into the correct ultrasonic signal. The drive and interrogation of the array is thus by means of the multiplexed bias voltage which opens "windows" during which the rf signal can be effective. The rf signal is turned off during the receive interval for a given channel in the usual manner.

The advantage of coupling the rf signal in this way are (i) the signal losses in the multiplexer are now only seen during the receive mode and (ii) the rf signal size is not limited by the multiplexer.

So far the present invention has been discussed in relation to the material from which the transducer elements are manufactured and this aspect of the invention is applicable irrespective of other steps in the manufacture of the ultrasonic transducer arrangement.

There will now be discussed a further aspect of the present invention which relates to the manufacturing process employed for producing an ultrasonic transducer array of the kind previously outlined, this further aspect being independent of the material employed for the manufacture of the transducer array elements.

One method of manufacturing an annular transducer array of the kind to which the present invention relates is disclosed in our European Patent No 0 671 221 in which the transducer array, and its associated multiplexer/control circuitry, is manufactured in-the-flat initially and then transformed into a cylindrical configuration.

In such a manufacturing method the functionally independent elements of the eventual annular array are produced by the following method.

A single block of PZT is mounted on a substrate in-the-flat. A plurality of saw cuts are then made in the PZT block to define the individual transducer elements of which there are typically sixty-four. The arrangement thus produced is then folded into the final cylindrical configuration to thus produce an annular ultrasonic transducer array made up of the plurality of transducer elements. In order to facilitate folding step, the aforementioned saw cuts are continued down to some extent into the polyimide substrate on which the transducer material is mounted. This extent is critical because it has to be sufficient to allow the assembly to be folded easily whilst at the same time not weakening the substrate to the point where it will fracture.

Because of the extremely small size of the arrangement just described the sawing step in the manufacturing process has to be carried out to extremely small tolerances. In addition, for the best operating characteristics, the saw cuts should have flat-bottoms but this is difficult to achieve in practice. The bottom of the saw cut is hereinafter referred to as the "slot bottom".

Therefore, according to a further aspect of the present invention in a manufacturing process for producing an ultrasonic transducer array in which a block of transducer material is divided into a plurality of discrete transducer elements and is mounted on a flexible substrate, flexing slots are formed in the substrate between adjacent transducer elements by means of a laser beam, This enables the depth of the cut to be more easily controlled, when compared with using a saw, and it also makes it possible to more easily approach the ideal rectangular shape for the bottom of the slot, or "slot bottom".

BRIEF DESCRIPTION OF THE DRAWINGS

How the invention may be carried out will now be described by way of example only with reference to the accompanying drawings in which.

DETAILED DESCRIPTION OF THE DRAWINGS

Figure 1:
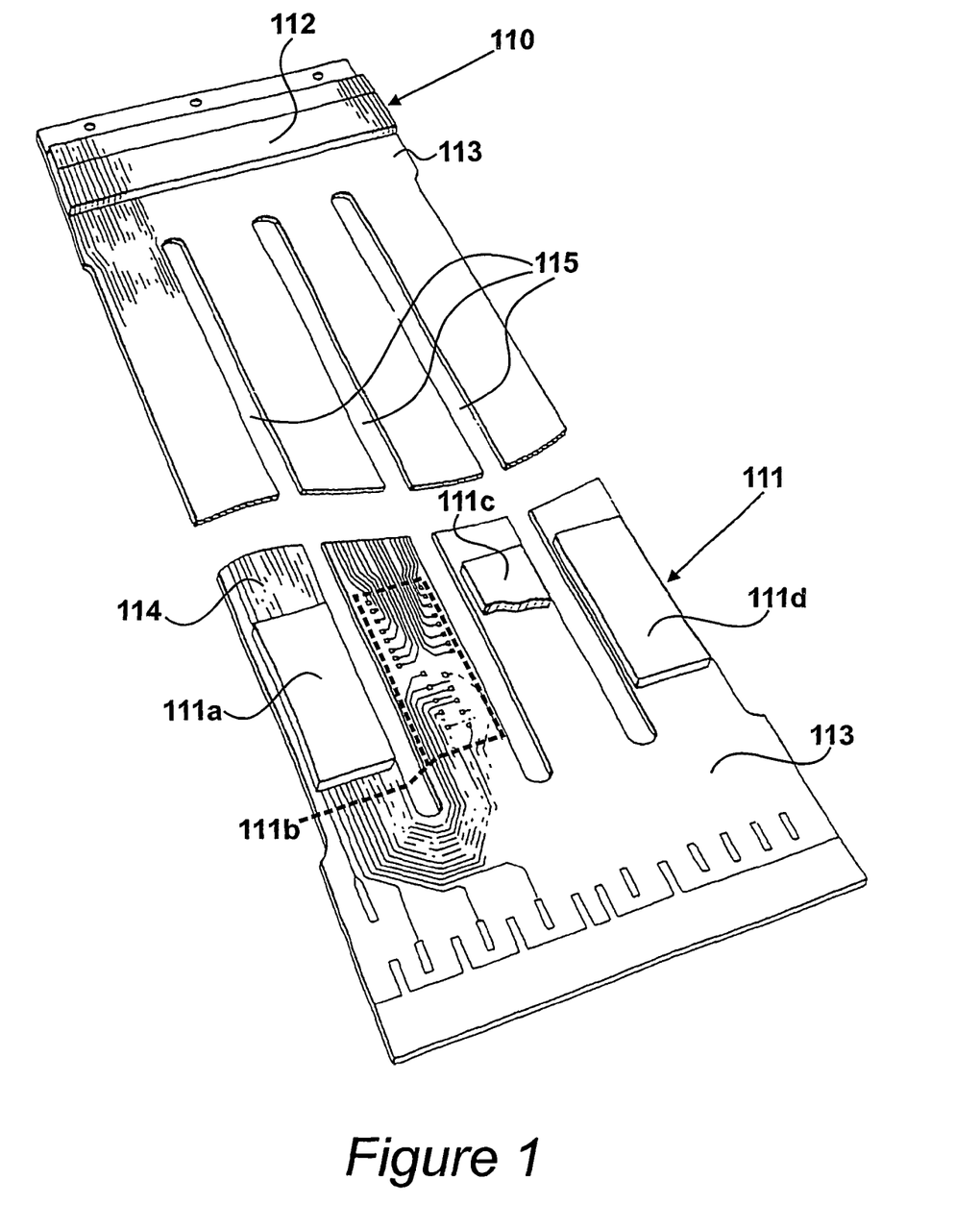
FIG. 1 is a perspective view of the ultrasonic transducer/multiplexer assembly in-the-flat as shown in FIG. 4 of the applicant's European Patent No 0 671 221.
Figure 2:
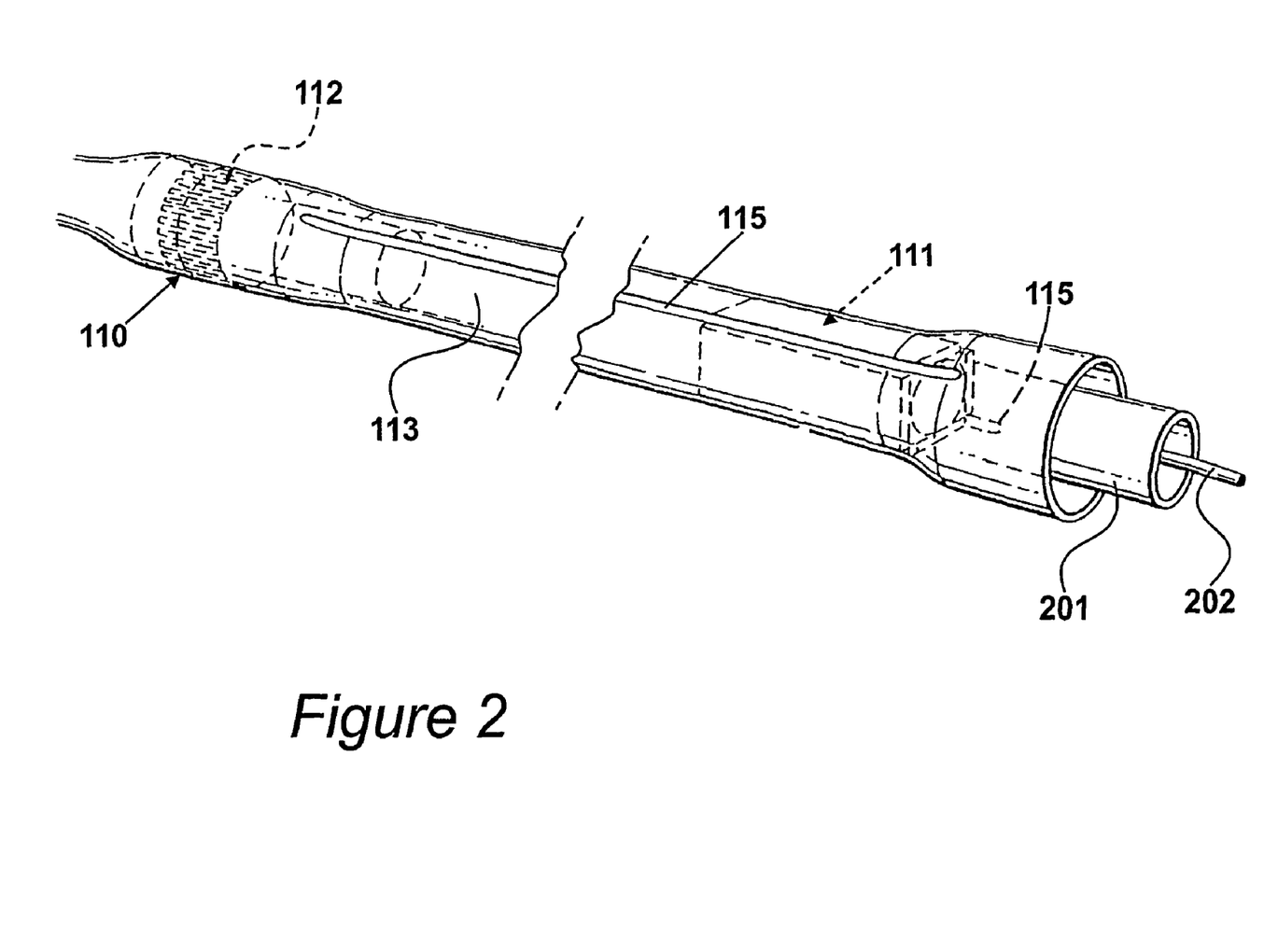
FIG. 2 is a perspective view of the assembly of FIG. 1 in its final cylindrical configuration as shown in FIG. 8 of the applicant's European Patent No 0 671 221.

FIGS. 1 and 2

A transducer array 110 and multiplexer 111 arrangement is first manufactured in-the-flat as shown in FIG. 1. It is then wrapped or rolled into the cylindrical configuration shown in FIG. 2.

The transducer array 110 comprises sixty four transducer elements 112 which are electrically connected to four 16-channels multiplexer chips 111a, 111b, 111c and 111d (111b being omitted for clarity and 111c being only partially shown) each chip being in the form of an integrated circuit.

The advantage of initially manufacturing the assembly shown in FIG. 1 in-the-flat is that it is easier to manufacture because firstly forming the various components in-the-flat rather than on a cylindrical surface is inherently easier and secondly it is possible to use standard production equipment. More particularly standard printed circuit and integrated circuit production methods can be employed. A further advantage, is that the thickness of flat material is easier to control to high accuracy than the wall thickness of cylindrical components.

The transducer array 110 consist of functionally discrete ceramic elements mounted on a flexible substrate 113.

Each multiplexer 111a, 111b, 111c and 111d, is in the form of an integrated circuit and this integrated circuit can itself be flip-chip bonded to a circuit comprising electrical connections 114 which are formed on the substrate 113 by means of known printed circuit techniques.

The transducer array 110 which consists of functionally discrete ceramic elements, is manufactured using the following steps.

The polyimide substrate material 113 is plated on both sides, with a 1-2 micron thickness of copper, typically by a two stage process in which vacuum deposition or sputtering is used to give a thin base coat of good allocation, and chemical plating techniques to increase the copper thickness to the desired value.

The conductive tracks 114 are then formed in the layer of copper on one side of the substrate by a standard photolithography technique followed by chemical etching or ion-beam milling to form the circuit pattern.

A block of piezo-electric material 112 having the desired radial thickness of the final transducer elements and coated on both sides by a metallisation layer, is bonded in one piece to an area of the copper layer which is shaped to define a connection pad on the substrate. The bonding is effected by a suitable adhesive which could comprise a low viscosity epoxy resin.

The polyimide substrate 113 has a copper layer on its bottom surface.

The piezo-electric transducer array, in use, would be energised through the copper layer, the upper metalised layer on the top of the piezoelectric ceramic transducer block 112 forming an earth return path and being electrically connected to the other copper layer to thus form a common return path.

The substrate 113 is provided with slots 115 to facilitate the folding or wrapping of the substrate into a cylindrical configuration as shown in FIG. 2.

In FIG. 2 the same reference numerals have been used as in FIG. 1 in order to designate the same items.

The cylindrical transducer array and multiplexer arrangement is mounted on a flexible plastic tubular body member 201 which itself is mounted on the main flexible plastic tubular body of the catheter (not shown). The usual guide wire is shown at 202.

Figure 3:
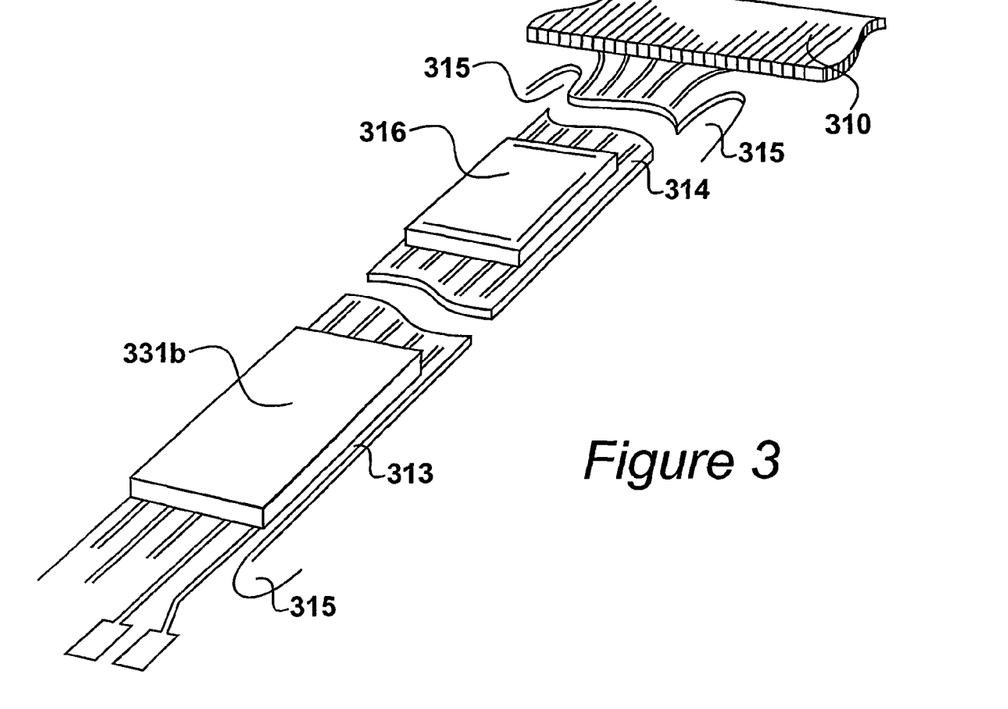
FIG. 3 is a fragmentary perspective view to an enlarged scale of one embodiment of the present invention showing part of a transducer array and associated multiplexer arrangement in the flat condition prior to its wrapping into the its cylindrical configuration.
Figure 4:
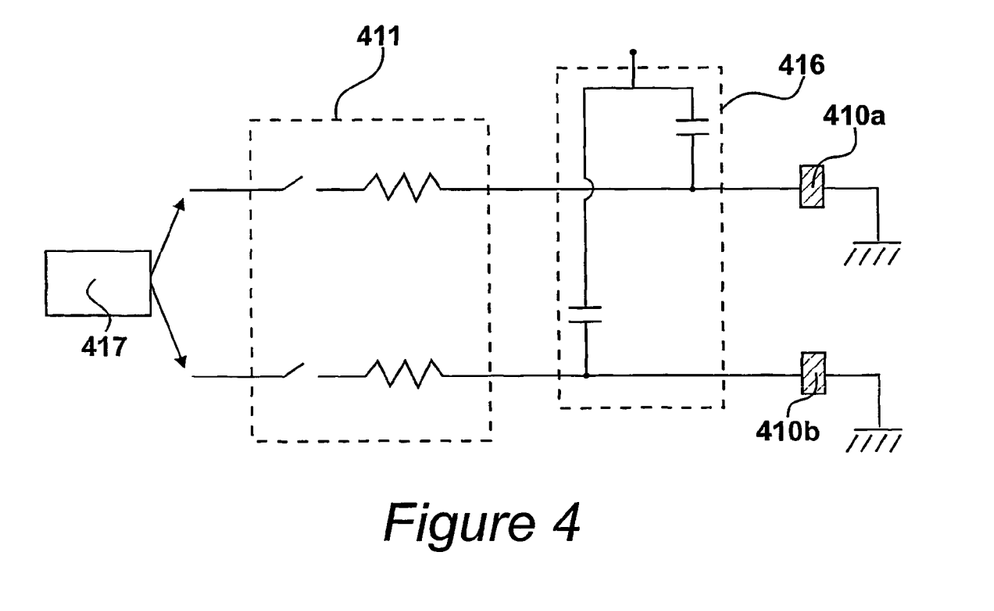
FIG. 4 illustrates the basic electronic address circuit employed with the present invention.

FIGS. 3 and 4

The transducer array and associated multiplexers are substantially the same in the present invention as those disclosed in our published European Patent No 0 671 221 and illustrated in FIGS. 1 and 2, except in the following respects.

The transducer array 310 itself is fabricated from a PMN (lead magnesium niobate) and the polyimide substrate 313 carries a block 316 of high permittivity low loss ceramic associated with each of the four multiplexers (only 331b is shown). Each block 316 functions as a common rf connection between the associated multiplexer and the associated group of sixteen transducer elements for coupling the rf signal to the transducer array input tracks 314. In a modification each ceramic block could be divided into sixteen physically articulated sections, one for each channel associated with each of the sixteen transducer elements. The block 316 capacitatively couples the multiplexer 331b to the individual channels of the array 310 by means of a high permittivity ceramic layer.

The transducer array 310 may be made from an electrostrictive or equivalent ferroelectric relaxor material.

The multiplexer arrangement is configured to transmit a DC bias voltage to the array 310.

FIG. 3 illustrates a single quadrant of the IVUS catheter and one method of coupling the rf signal to the array. This method is directly applicable to the existing configuration of the "wrap". The principle of operation is as follows. PMN requires a bias field to become significantly piezoelectric and thus the PMN elements only transmit and receive when the bias voltage is applied through the multiplexer. The rf signals can therefore be applied simultaneously (but not continuously) to all elements of the array 310; because only those transducer elements which have the bias field applied to them will transform the rf signal into an ultrasonic signal. The drive and interrogation of the array 310 is thus by means of the multiplexed bias voltage which opens windows during which the rf signal can be effective. Clearly the rf signal but not the dc bias is turned off during the receive interval for a given channel. Advantages of coupling the rf signal in this way are (i) the signal losses in the multiplexer are now only seen in receive and (ii) the rf signal size is not limited by the multiplexer. FIG. 4 shows the essentials of the electronic addressing of two channels of the array.

FIG. 4 illustrates part of the control circuit for two of the transducer elements 410a and 410b.

The multiplexer 411 is configured to transmit a DC bias voltage 417 to the elements 410a and 410b of the array.

The high permittivity ceramic block 416 functions as a common rf connection between the multiplexer 411 and the array and capacitatively couples the latter to the former. U PZT can act as such a component.

FIGS. 5 to 10

Existing array-dicing processes have problems with height-control and the shape of the slot bottom. The height-control problem is exacerbated by:

(i) the non-uniformity of the polyimide substrate;

(ii) the difficulties of vacuum-mounting an undulating, flexible substrate containing rigid components with stressed adhesive interfaces; and (iii) dicing-blade wear. The slot bottom problem relates primarily to the rounded shape of the cutting edge of the dicing blade which is reproduced approximately in the array slot-bottom.

Flat-bottomed blades are difficult to achieve in practice because both the blade-dressing procedure prior to dicing and the blade-wear of the dicing process itself tend to yield a rounded blade-edged profile. The rounded profile, leading to a similar shape in the polyimide slot bottom, is undesirable from the point of view of the wrap-mechanics and acoustic performance of the final array. Furthermore, any subsequent processing of a saw-cut polyimide slot bottom (e.g. by laser ablation) would necessarily begin from the "parabolic" shape left by the sawing process, and may not result in the desired rectangular shape. The process issues to be addressed are therefore:

(i) how can shape-controlled slots be cut into a thin, flexible and variable carrier film?

(ii) can a pre-cut flex-circuit slot bottom, be ablated accurately using the flex-circuit itself as a mask?

The present invention relates to the fabrication of rectangular slot bottoms in the polyimide substrate by a laser ablation process prior to array dicing. The flex-circuit slot bottom is ablated using the flex-circuit itself as a mask, which automatically aligns the slot bottoms with the flex-circuit.

The following process achieves a rectangular slot bottom in the polyimide.

Figure 5:
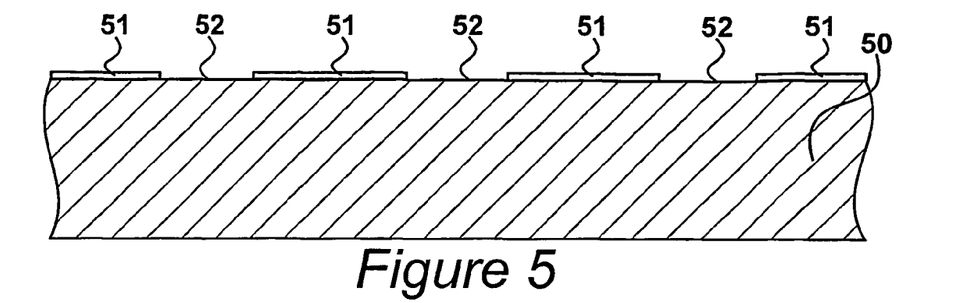
FIGS. 5 to 10 illustrate the various stages, according to the present invention, for forming the slot bottoms in the ultrasonic transducer.
Figure 6:
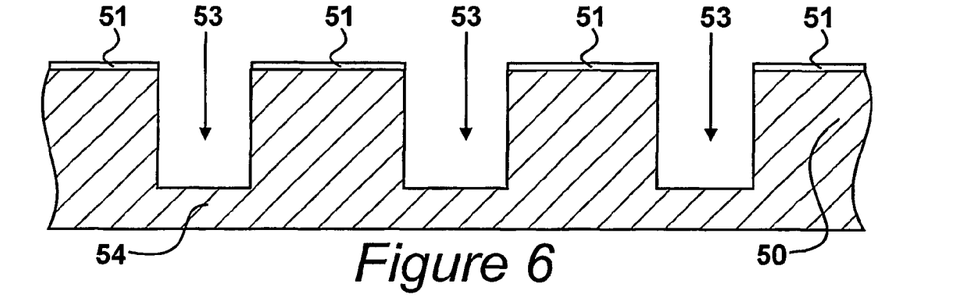

The flex-circuit is utilised as a mask for laser ablation. The transducer area of the flex-circuit contains copper tracks 51 of width equal to the element width, namely 30 μm formed in a polyimide matching layer 50. These tracks 51 in conjunction with a rectangular aperture step 52, defining an overall exposure window, are used as a mask for laser ablation of rectangular trenches 53 of width ~17 μm in the polyamide flex-circuit. The intensity-time exposure parameters for the laser yield reproducible slot bottoms 54. It may be advantageous to thicken the tracks 51 to 1-2 μm by use of nickel plating in the transducer area, as on the remainder of the flex-circuit.

Figure 7:
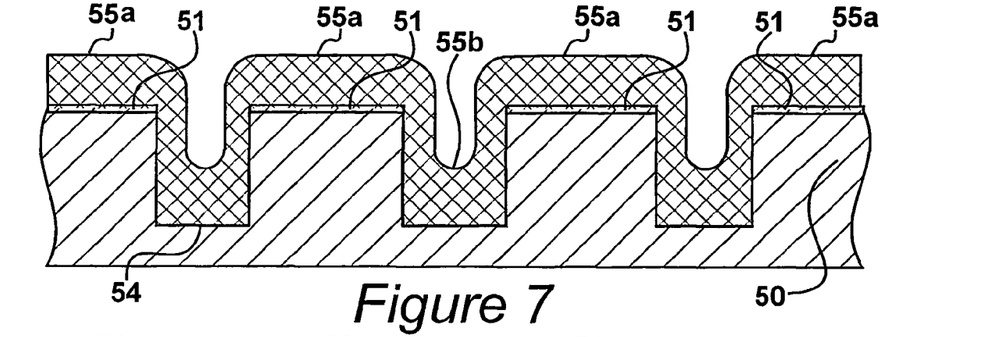

The whole flex-circuit 51 is coated with a layer of photoresist 55 ~5 μm thick using a spinning technique, giving the result illustrated in FIG. 7. It is only necessary that the trenches 53 be partly filled with the photoresist material 55.

Figure 8:
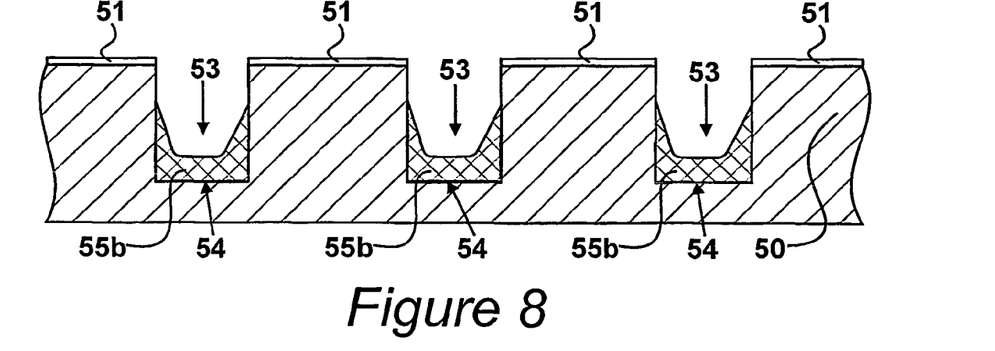

The photoresist layer 55 is ablated and the ~5 μm thick layer 55a covering the metal tracks 51 is removed. This will leave a photoresist layer 55b in the trench-bottoms, as illustrated in FIG. 8. The same result can also be achieved by "wicking" photoresist (or an alternative slot bottom fill substance) along the trenches (i.e. relying on capillary action to cause the resist to move along the trenches to substantially fill them) from one end, or by selective ultra violet curing of the photoresist layer means of an auxiliary mask.

Figure 9:
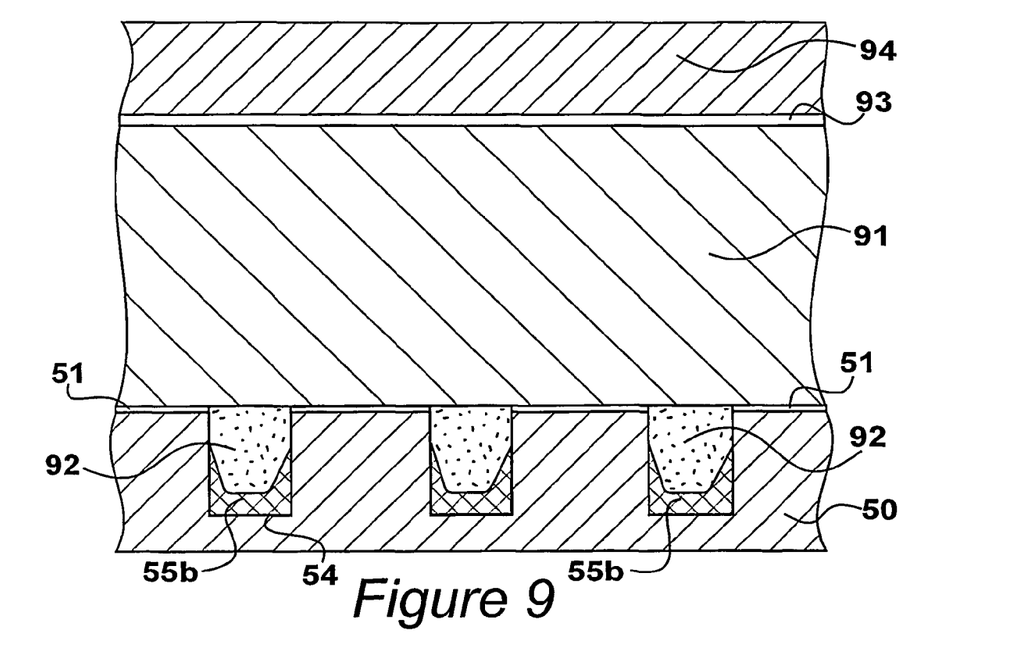
Figure 10:
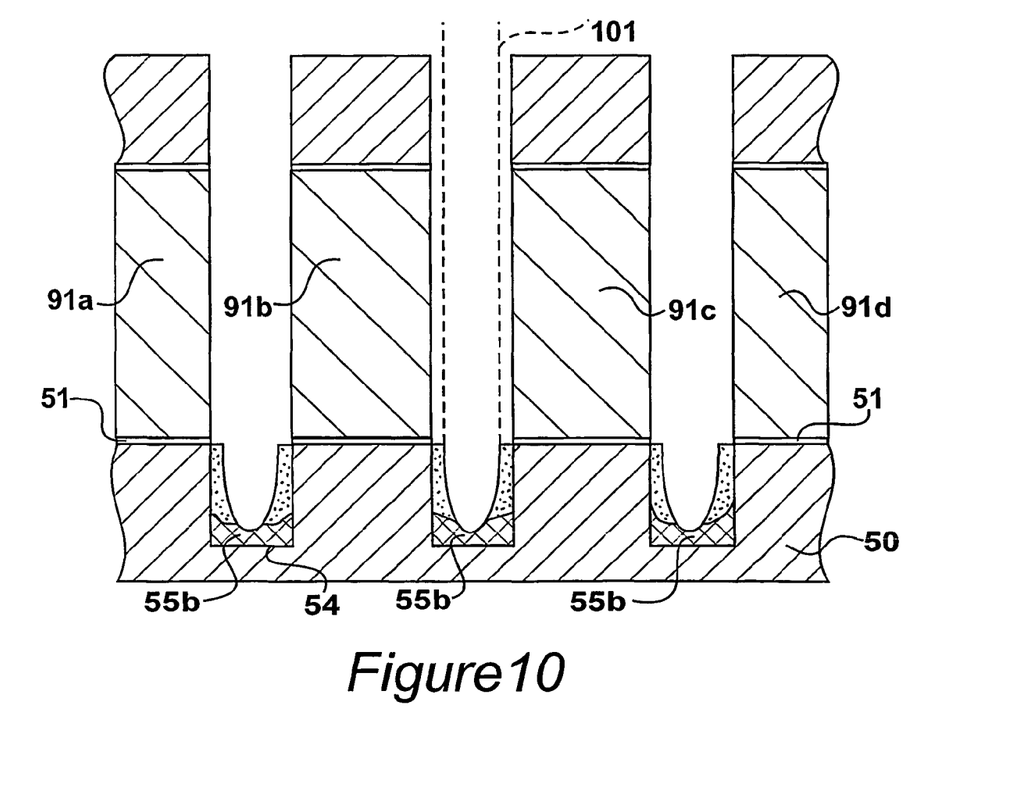

Having accurately formed the slot bottom 54 using a laser (FIGS. 5 to 8), the PZT transducer array is then fabricated on top of the arrangement shown in FIG. 8. This fabrication is illustrated in FIGS. 9 and 10.

A PZT block 91 is bonded by adhesive 92 to the layer 50 using known adhesive techniques. This is illustrated in FIG. 9. The adhesive 92 will fill the trenches 54 above the photoresist layer 55b and will not penetrate to the bottom of the slot bottom 91a, 91b, 91c, 91d etc. There is an upper metallisation layer 93 topped by a polyimide ground plane 94.

The individual PZT elements of the transducer array are diced in the normal way using a diamond saw to create the slots, ensuring the blade penetrates the polyimide by approximately two thirds of its kerf depth (e.g. 10 μm if the polyimide kerf is 15 μm deep). This is illustrated in FIG. 10, and shows the saw cuts penetrating into the temporary key-fill material (photoresist) 55b, the saw being indicated at 101 in broken lines.

The polyimide slot bottoms are cleaned with a suitable solvent to remove the residual photoresist 55b and create an empty flat bottomed slot bottom.

The advantages of the modified process are the following:

(i) A reproducible slot bottom can be created in the polyimide without melting or tearing of the plastic and without the risk of depth overshoot inherent in the existing sawing process. That is, the laser will ablate a certain thickness of polyimide irrespective of whether or not the flex-circuit is flat, whereas the sawing process depends critically on mounting-fixture flatness, flex circuit planarity and flex-circuit thickness variability.

(ii) A rectangular slot bottom is the optimum for strain relief on wrapping and leads to significantly reduced risk of PZT fracture of wrapping stresses.

(iii) A rectangular slot bottom is in many cases the optimum for reduction of acoustic cross-talk.

(iv) The modified process removes the need for stringent height-control in the dicing process, and thus removes a demanding process parameter involving significant cost.

As a further aspect of the present invention there will now be described a modification of the transducer fabrication technique which could address both the shape and depth of the slot bottom.

This modified method is as follows:

(i) Double-metalize the ground-plane polyimide and wax both this and the ceramic spacer material to a ceramic carrier block. The ceramic carrier will be a low-density, low-cost PZT material, or some other machineable ceramic such as Macor or Shapal. The wax will be of a type soluble in a safe organic solvent, and capable of being pressed under controlled, elevated-temperature, conditions into a thin, uniform layer.

(ii) Bond the pre-poled, metalized, transducer block, of dimensions 3.2×0.8×0.05, to the ground-plane electrode and, the ground-plane electrode to the spacer using Hysol epoxy in a purpose-built assembly press.

(iii) Dice the transducer block whilst on the sacrificial ceramic carrier. The slot bottom depth will be such as to penetrate the ceramic carrier by a few tens of microns. By this means parallel-sided cuts in the PZT and ground-plane are achieved and each full array width is defined.

(iv) Invert the ceramic carrier block, ground-planes and transducer plates over the polyimide matching layer (flex-circuit) and epoxy bond in a temperature and pressure controlled press. This step involves accurate alignment of the transducer array and the flex-circuit. The alignment is achieved by dicing through the carrier ceramic block at, or close to, the perimeter of the transducer array, in order to allow the individual positioning of these arrays on the flex-circuit diaphragm. Alternative bonding processes are flip-chip solder and indium-gold. Epoxy-bonding would involve excess adhesive which may interfere with the laser ablation process.

(v) Remove the ceramic carrier by immersion of the flex-circuit in the chosen solvent. Remaining on the flex-circuit are the diced PZT arrays with their diced ground-planes, each array bonded to the polyimide flex circuit. Since the exposed surface of the ground-plane is metalized it acts as a reflector of the laser beam, whereas the polyimide does not.

(vi) Use the diced PZT-array and ground-plane assembly as a mask for ablation of the polyimide flex-circuit. Since the exposed surface of the ground-plane is metalized it acts as a reflector of the laser beam, whereas the polyimide in the slot bottom is exposed to the full-power of the laser and is ablated. Clearly, since the slot bottom shape is rectangular before ablation, there is a much greater chance of controlling the thinning to give, say, a 0.005 uniform layer of polyimide remaining after ablation. An alternative to this is to ablate the flex circuit before assembly using the tracks in the transducer area as a mask.

The invention claimed is:

1. An apparatus for intravascular ultrasonic imaging, the apparatus comprising:
    a flexible elongate member sized for insertion within a vasculature;
    an ultrasonic transducer array, mounted proximate a distal end of the flexible elongate member, wherein transducer elements of the ultrasonic transducer array comprise a non-polymeric electrostrictive material;
    a high permittivity ceramic member that signally couples a common radiofrequency signal source to all elements of the transducer array simultaneously; and
    a controller configured to cause the common radiofrequency signal to be provided through the ceramic member to all the transducer elements of the ultrasonic transducer array and cause a bias field to be selectively transmitted to one or more of the transducer elements such that only transducer elements having the bias field applied to them will transform the common radiofrequency signal into an ultrasonic signal.

2. The apparatus of claim 1 wherein the electrostrictive material is a relaxor ferroelectric material.

3. The apparatus of claim 2, wherein the electrostrictive material comprises lead magnesium niobate.

4. The apparatus of claim 1, wherein the controller is controls are configured to transmit and receive signals only while the bias voltage is applied.

5. The apparatus of claim 1 further comprising a multiplexer arrangement through which elements of the transducer array are selectively energized and through which echo signals received by the transducer array arc passed to the proximal end of the flexible elongate member.

6. The apparatus of claim 5 wherein the multiplexer arrangement comprises a plurality of integrated circuits.

7. The apparatus as claimed in claim 6 wherein the transducer array is arranged in a substantially cylindrical configuration.

8. The apparatus of claim 6 wherein adjacent integrated circuits arc spaced from one another by a slot.

9. The apparatus of claim 6 wherein the integrated circuits are flip-chip bonded to an electrical circuit.

10. The apparatus of claim 9 wherein the electrical circuit comprises a printed circuit.

11. The apparatus of claim 1 wherein the transducer array comprises:
    a substrate;
    electrically conductive tracks on the substrate; and
    a set of individual transducer array elements created by forming slots in a piezoelectric block.

12. The apparatus of claim 11, further comprising at least one multiplexer circuit coupled to the electrically conductive tracks.

13. The apparatus of claim 11, further comprising slot bottoms formed in the substrate adjacent the electrically conductive tracks.

14. The apparatus of claim 13, wherein the slot bottoms are formed with a laser.

15. The apparatus of claim 1 wherein the flexible elongate member is a catheter.

16. The apparatus of claim 1 wherein the high permittivity ceramic member capacitatively couples the common radiofrequency signal source to signal lines that selectively carry a DC bias voltage signal to individual ones of the elements of the transducer array.

17. The apparatus of claim 16 wherein a multiplexer selectively provides the DC bias voltage signal to individual ones of the transducer elements of the transducer array.

18. The apparatus of claim 16 wherein the electrostrictive material of the transducer elements comprises ferroelectric relaxor material.

19. The apparatus of claim 16 wherein the electrostrictive material of the transducer elements comprises lead magnesium niobate.

20. An apparatus for intravascular ultrasonic imaging, the apparatus comprising:
    a flexible elongate member sized for insertion within a vasculature;
    an ultrasonic transducer array mounted proximate a distal end of the flexible elongate member, the array comprising a plurality of ultrasonic transducer elements, each comprising a non-polymeric electrostrictive material;
    a multiplexer configured to selectively transmit a DC bias voltage to the plurality of ultrasonic transducer elements;

a common high permittivity ceramic member configured to simultaneously electrically couple all the transducer elements to each other and to a common radiofrequency signal source; and a controller configured to cause the common radiofrequency signal to be provided through the ceramic member to all of the transducer elements of the ultrasonic transducer array and cause a bias field to be selectively transmitted to one or more of the transducer elements such that only transducer elements having the bias field applied to them will transform the common radiofrequency signal into an ultrasonic signal.

21. A method for intravascular ultrasonic imaging, the method comprising:

providing an apparatus comprising:
- a flexible elongate member sized for insertion within a vasculature;
- an ultrasonic transducer array mounted proximate a distal end of the flexible elongate member, the array comprising a plurality of ultrasonic transducer elements;
- a multiplexer configured to selectively transmit a DC bias voltage to the plurality of ultrasonic transducer elements; and
- a common ceramic member configured to simultaneously electrically couple all the transducer elements to each other and to a common radiofrequency signal source;

simultaneously providing an RF signal through the common ceramic member to all the ultrasonic transducer elements; and selectively transmitting a bias field to the transducer elements, such that only transducer elements having the bias field applied to them will transform the rf signal from the common ceramic member into an ultrasonic signal.

22. The method of claim 21, further comprising turning off the RF signal to all transducer elements without turning off the bias field during a receive signal for a given channel.

* * * * *